US009839713B2

(12) United States Patent
Johns et al.

(10) Patent No.: US 9,839,713 B2
(45) Date of Patent: Dec. 12, 2017

(54) DRY ACID COMPOSITION AND USES THEREOF

(71) Applicant: Chemtrade Logistics Inc., Toronto (CA)

(72) Inventors: Rex Johns, Jonesboro, AR (US); Levi Grove, Fairview Heights, IL (US)

(73) Assignee: CHEMTRADE LOGISTICS INC., Toronto (CA)

( * ) Notice: Subject to any disclaimer, the term of this patent is extended or adjusted under 35 U.S.C. 154(b) by 0 days.

(21) Appl. No.: 14/714,890

(22) Filed: May 18, 2015

(65) Prior Publication Data
US 2015/0343108 A1   Dec. 3, 2015

Related U.S. Application Data

(60) Provisional application No. 62/004,316, filed on May 29, 2014.

(51) Int. Cl.
*A61L 9/01* (2006.01)
*A61L 9/014* (2006.01)

(52) U.S. Cl.
CPC ................ *A61L 9/01* (2013.01); *A61L 9/014* (2013.01)

(58) Field of Classification Search
USPC ........................................................ 424/76.6
See application file for complete search history.

(56) References Cited

U.S. PATENT DOCUMENTS

| | | | | |
|---|---|---|---|---|
| 2,895,873 | A | * | 7/1959 | Sawyer, Jr. .......... A01K 1/0154 119/173 |
| 3,029,783 | A | * | 4/1962 | Sawyer, Jr. .......... A01K 1/0154 119/171 |
| 5,176,879 | A | * | 1/1993 | White .................. A01K 1/0152 119/171 |
| 5,622,697 | A | | 4/1997 | Moore |
| 5,865,143 | A | | 2/1999 | Moore |
| 5,914,104 | A | | 6/1999 | Moore |
| 5,928,403 | A | | 7/1999 | Moore |
| 5,960,743 | A | | 10/1999 | Taylor |
| 5,961,968 | A | | 10/1999 | Moore |
| 6,029,603 | A | | 2/2000 | Evans |
| 6,468,518 | B2 | | 10/2002 | Lind |
| 6,530,343 | B1 | | 3/2003 | Lind |
| 7,011,824 | B2 | | 3/2006 | Moore |
| 9,301,440 | B1 | | 4/2016 | Moore, Jr. |

FOREIGN PATENT DOCUMENTS

WO   WO2011131629   * 10/2011

OTHER PUBLICATIONS

Moore et al., "Effect of Chemical Amendments on Ammonia Volatilization from Poultry Litter," J. Environ. Qual. 24: 293-300 (1995).
McWard and Taylor, "Acidified Clay Litter Amendment," J. Appl. Poultry. Res., 9:518-529 (2000).
Wang et al. "Reducing potential leaching of phosphorus, heavy metals, and fecal coliform from animal wastes using bauxite residues," Water, Air & Soil Pollution, 214(1-4)241-252 (2011).

* cited by examiner

*Primary Examiner* — Devang Thakor
(74) *Attorney, Agent, or Firm* — Polsinelli PC (57) ABSTRACT

The present disclosure provides dry compositions and methods for using the dry compositions to treat animal facilities. In particular, a dry composition comprises an acid, which provides an immediate source of protons, and a process residue comprising alum and a material comprising reactive aluminum, each of which provides a delayed source of protons.

49 Claims, 1 Drawing Sheet

DRY ACID COMPOSITION AND USES THEREOF

CROSS-REFERENCE TO RELATED APPLICATIONS

This application claims the priority of U.S. Provisional Application No. 62/004,316, filed May 29, 2014, which is hereby incorporated by reference in its entirety.

FIELD

The present disclosure relates to dry compositions and methods for using to the dry compositions to treat animal facilities.

BACKGROUND

Airborne ammonia in animal facilities is detrimental to the health of both the animals and the farm workers. The gas results from the decomposition of animal wastes, and its formation is influenced by litter moisture, pH, and temperature. Thus, the main factors affecting the levels of ammonia in animal facilities are the litter conditions and the amount of ventilation. Litter amendments have been developed that acidify the litter and inhibit ammonia volatilization. For example, dry alum (aluminum sulfate) provides excellent ammonia control (i.e., acidifies the litter and suppresses ammonia volatilization), but has the drawback that it requires adequate litter moisture and time for activation. Other litter treatments contain sulfuric acid, which provides immediate acidification and ammonia control without an activation step, but the ammonia control is short lived. Dry litter amendments are less hazardous to handle and easier to apply than liquid litter amendments. What is needed, therefore, is a dry litter amendment that provides both immediate and extended ammonia control.

SUMMARY

One aspect of present disclosure is the provision of a dry composition comprising a process residue comprising alum, an acid, and a material comprising reactive aluminum. The acid provides an immediate source of protons, and the process residue comprising alum and the material comprising reactive aluminum provide delayed sources of protons.

Another aspect of the disclosure encompasses a method for treating an animal facility. The method comprises applying a dry composition to a surface of the animal facility to form a treated animal facility. The dry composition comprises a process residue comprising alum, an acid, and a material comprising reactive aluminum.

A further aspect of the present disclosure provides a method for treating a surface that contacts or will contact animal wastes. The method comprises applying a dry composition to the surface to form a treated surface. The dry composition comprises a process residue comprising alum, an acid, and a material comprising reactive aluminum.

Still another aspect of the present disclosure encompasses a method for treating an animal litter. The method comprises applying a dry composition to the animal litter to form a treated animal litter. The dry composition comprises a process residue comprising alum, an acid, and a material comprising reactive aluminum.

Other aspects and iterations of the disclosure are described in more detail below.

DETAILED DESCRIPTION

Provided herein are dry compositions and methods for using the dry compositions. A dry composition comprises a process residue comprising alum, an acid, and a material comprising reactive aluminum. The dry compositions disclosed herein have two key properties. First, the dry compositions are solid compositions comprising particles, granules, grains, or fragments of said dry composition. Second, the dry compositions comprise immediate and delayed sources of protons. In particular, the acid of the dry composition provides an immediate source of protons, and the process residue comprising alum (i.e., aluminum sulfate) and/or the material comprising reactive aluminum provide delayed sources of protons. Thus, the dry compositions have immediate onsets of activity as well as prolonged durations of action. Among the various uses for the dry compositions include their use for reducing the pH of animal litter, reducing ammonia volatilization from animal litter, reducing moisture levels in animal litter, increasing the nitrogen content of animal litter for improved fertilizer value, reducing the runoff of soluble phosphorous from animal litters, and/or reducing animal stress.

(I) Dry Composition

One aspect of the present disclosure encompasses a dry composition comprising an acid, a process residue comprising alum, and a material comprising reactive aluminum. Each of the components and properties of the dry composition are detailed below.

(a) Components (i) Acids

The dry composition comprises an acid or a combination of acids. The acid provides an immediate or readily available source of protons. Suitable acids include those having pKa values of about 3.0 or less, and include, without limit, sulfuric acid, hydrochloric acid, hydrobromic acid, hydroiodic acid, nitric acid, phosphoric acid, perchloric acid, chloric acid, fluorosulfuric acid, fluoroboric acid, hexafluorophosphoric acid, methanesulfonic acid, ethanesulfonic acid, benzenesulfonic acid, p-toluenesulfonic acid, trifluoromethanesulfonic acid, or combinations thereof. In some embodiments, the acid may be hydrochloric acid. In specific embodiments, the acid may be sulfuric acid. In additional embodiments, the composition may comprise a combination of sulfuric acid and hydrochloric acid.

The amount of acid included in the composition can and will vary depending, for example, on the other components of the dry composition and the desired functional properties of the dry composition. In some embodiments, the amount of acid included in the composition may range from about 30% to about 65% by weight of the composition. In specific embodiments, the amount of acid included in the composition may range from about 40% to about 60% by weight of the composition The amount of free acid present in the dry composition may range from about 3% to about 20% by weight of the dry composition. In some embodiments, the amount of free acid present in the dry composition may range from about 4% to about 18%, or from about 5% to about 16% by weight of the dry composition. In specific embodiments, the amount of free acid present in the dry composition may range from about 6% to about 14% by weight of the dry composition.

The acid also provides anions to the dry composition. In certain embodiments, the level of anions present in the dry composition may range from about 25% to about 55% by weight of the dry composition. In other embodiments, the level of anions present in the dry composition may range from about 30% to about 50% by weight of the dry composition. In specific embodiments, the level of anions present in the dry composition may range from about 35% to about 45% by weight of the dry composition.

(ii) Process Residues Comprising Alum

The dry composition also comprises a process residue comprising alum (i.e., aluminum sulfate) that serves as a carrier material for the acid of the composition. In general, the process residue comprising alum is a co-product of commercial alum production and is the solid material that remains after removal of most of the alum from bauxite (an aluminum ore) or high alumina clay. The alum production process comprises reacting bauxite or high alumina clay with sulfuric acid to form alum. The process residue comprising alum present in the composition may be alum process residue (APR), alum mud (AM), high clay alumina (HCA), or a combination thereof.

In general, the process residue comprising alum comprises from about 0.5% to about 10% of alum by weight of the process residue. In certain embodiments, the amount of alum present in the process residue may range from about 0.5% to about 2%, from about 2% to about 4%, from about 4% to about 6%, or from about 6% to about 10% by weight of the process residue. In some embodiments, the amount of alum present in the process residue may range from about 1% to about 6% by weight of the process residue. In specific embodiments, the amount of aluminum sulfate present in the process residue may range from about 2% to about 4% by weight of the process residue.

The process residue comprising alum generally also comprises water. The amount of water present in the process residue comprising alum may range from about 15% to about 40% by weight of the process residue. In various embodiments, the amount of water present in the process residue may range from about 15% to about 20%, from about 20% to about 25%, from about 25% to about 30%, from about 30% to about 35%, or from about 35% to about 40 by weight of the process residue. In specific embodiments, the amount of water present in the process residue may range from about 20% to about 35% by weight of the process residue.

Depending upon the source of the aluminum ore used in the commercial alum production process, the process residue comprising alum may further comprise aluminum oxide, aluminum hydroxide, iron oxide, titanium dioxide, silica, alumina, kaolinite, gibbsite, boehmite, diaspore, quartz, hematite, magnetite, siderite, goethite, and/or other insoluble materials.

The amount of the process residue comprising alum included in the composition can and will vary depending on the amount of alum in the process residue and/or the desired functional properties of the dry composition. In general, the amount of process residue comprising alum present in the composition ranges from about 30% to about 60% by weight of the composition. In various embodiments, the amount of the process residue comprising alum present in the composition may range from about 30% to about 35%, from about 35% to about 40%, from about 40% to about 45%, from about 45% to about 50%, from about 50% to about 55%, or from about 55% to about 60% by weight of the composition. In specific embodiments, the amount of the process residue comprising alum present in the composition may range from about 40% to about 50% by weight of the composition. In other embodiments, the amount of the process residue comprising alum present in the composition may range from about 45% to about 55% by weight of the composition.

The process residue comprising alum provides a delayed source of protons. First, upon contact with water, the alum (i.e., aluminum sulfate) in the process residue undergoes hydrolysis to form buffered aluminum hydroxide intermediates and protons. Second, the process residue also may further comprise aluminum hydroxide/oxide that, in the presence of acid, can be converted to acidic aluminum salts, which then, in the presence of water, can be hydrolyzed to form buffered aluminum hydroxide intermediates and additional protons.

(iii) Materials Comprising Reactive Aluminum

The dry composition also comprises a material comprising reactive aluminum. As used herein, the term "reactive aluminum" refers to aluminum oxide ($Al_2O_3$), aluminum hydroxide ($Al(OH)_3$), aluminum oxide hydroxide ($AlO(OH)$), or combinations thereof. Without being bound by any specific theory, it is believed that the reactive aluminum may react with acid that may be present on the surface of the dry composition to form an acidic aluminum salt, thereby neutralizing the surface of the dry composition. For example, in embodiments in which the acid is sulfuric acid, the sulfuric acid can react with the reactive aluminum to form alum (aluminum sulfate).

A variety of materials comprising reactive aluminum may be included in the dry composition. Suitable materials include, but are not limited to, bauxite, aluminum ore, high alumina clay, aluminum silicate, gibbsite, boehmite, diaspore, aluminum trihydrate, alumina, calcinated alumina, corundum, or a combination thereof. In specific embodiments, the material comprising reactive aluminum may be bauxite.

The amount of the material comprising reactive aluminum included in the composition can and will vary depending on the other components in the composition and/or the desired functional properties of the composition. In general, the amount of the material comprising reactive aluminum included in the composition ranges from about 1% to about 15% by weight of the composition. In various embodiments, the amount of the material comprising reactive aluminum present in the composition may range from about 1% to about 4%, from about 4% to about 6%, from about 6% to about 8%, from about 8% to about 10%, or from about 10% to about 15% by weight of the composition. In specific embodiments, the amount of the material comprising reactive aluminum present in the composition may range from about 4% to about 6% by weight of the composition.

The amount of aluminum oxide ($Al_2O_3$) present in the dry composition can and will vary depending upon the source of the material comprising reactive aluminum. In some embodiments, the level of aluminum oxide may range from about 3% to about 20% by weight of the dry composition. In certain embodiments, the amount of aluminum oxide present in the dry composition may range from about 4% to about 18%, or from about 5% to about 16% by weight of the dry composition. In specific embodiments, the amount of aluminum oxide present in the dry composition may range from about 6% to about 14% by weight of the dry composition.

The material comprising reactive aluminum also provides a delayed source of protons. Reaction of the reactive aluminum with protons can generate acidic aluminum salts, which, in the presence of water, can be hydrolyzed to form buffered aluminum hydroxide intermediates and additional protons.

(iv) Water Content of the Dry Composition

In general, the dry composition disclosed herein has a water content of about 30% or less by weight of the dry composition. In various embodiments, the dry composition may have less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, less than about 1%, or less than about 0.01% of water by weight of the dry composition. In some embodiments, the dry composition disclosed herein has less than about 10% of water by weight of the composition. In specific embodiments, the dry composition disclosed herein has less than about 5% of water by weight of the dry composition.

(v) Optional Additional Ingredients

The dry composition may also comprise optional additional ingredients. In some embodiments, the composition may be supplemented with additional alum. The alum may be dry alum or liquid alum. The amount of supplemental alum may range from about 1% to about 30% by weight of the dry composition. In certain embodiments, the amount of supplemental alum added to the dry composition may range from about 1% to about 5%, from about 5% to about 10%, from about 10% to about 20%, or from about 20% to about 30% by weight of the dry composition.

In other embodiments, the dry composition may further comprise an additional ingredient chosen from aluminum hydrate, aluminum clay, lime, soda ash, caustic potash, caustic soda, or combinations thereof. The amount of the additional ingredient(s) may range from about 1% to about 30% by weight of the dry composition. In certain embodiments, the composition may comprise from about 1% to about 5%, from about 5% to about 10%, from about 10% to about 20%, or from about 20% to about 30% of aluminum hydrate, aluminum clay, lime, soda ash, caustic potash, caustic soda, or combinations thereof by weight of the dry composition.

(b) pH and Ammonia Binding Capacity

The pH of the dry composition disclosed herein can and will vary depending upon the identity of its components. In general, the dry composition has a pH of at least 1.0. In various embodiments, the dry composition may have a pH of about 1.0, about 1.25, about 1.5, about 1.75, about 2.0, about 2.5, or about 3.0.

The dry composition provides protons that lower the pH of the surface and/or the surrounding area to which the dry composition is applied. In some embodiments, the protons can react with (or bind to) ammonia, thereby forming ammonium. Thus, the dry composition has an ammonia binding capacity. In general, the ammonia binding capacity of the dry composition is at least 5 g of ammonia per 100 g of the dry composition (i.e., at least 5%). In various embodiments, the ammonia binding capacity of the dry composition may be at least about 6 g, at least about 7 g, at least about 8 g, at least about 9 g, at least about 10 g ammonia, at least about 11 g ammonia, at least about 12 g, at least about 13 g, at least about 14 g, or at least about 15 g of ammonia per 100 g of the dry composition.

(c) Physical Form of the Dry Composition

The dry composition is a solid comprising particles, granules, grains, fragments, or similar solid units. In specific embodiments, the dry composition may be a granular material. In some embodiments, the particles of the granular material may have a size distribution that allows them to pass through a US standard mesh No. 5 (4.0 mm), 6 (3.35 mm), 7 (2.80 mm), 8 (2.36 mm), 10 (2.0 mm), 12 (1.7 mm), or 14 (1.4 mm) sieve. In specific embodiments, the particles of the granular material may have a size distribution that allows them to pass through a US s standard mesh No. 10 commercial sieve.

(d) Specific Embodiments

In specific embodiments, the dry composition comprises alum process residue (APR) as the process residue comprising alum, sulfuric acid as the acid, and bauxite as the material comprising reactive aluminum. The APR included in the dry composition may comprise from about 2% to about 4% of alum and an initial water content from about 20% to about 35% by weight of the APR. The resultant dry composition may comprise from about 5% to about 16% of free sulfuric acid, from about 35% to about 45% of sulfate, from about 5% to about 16% of aluminum oxide, and about 5% or less of water by weight of the dry composition. The amount of APR present in the dry composition may range from about 45% to about 55%, and the amount of bauxite present in the composition may range from about 4% to about 6% by weight of the dry composition. The dry composition may have a pH from about 1 to about 2.

(II) Processes for Producing the Dry Composition

Another aspect of the disclosure encompasses processes for producing the dry compositions described above in section (I). In general, the process comprises (a) mixing the components, which are detailed above in section (I)(a), to form a mixture and (b) drying the mixture to produce the dry composition.

(a) Ratio of Components

The weight ratio of the components comprising the dry composition, i.e., the process residue comprising alum, the acid, and the material comprising reactive aluminum, can and will vary depending upon the identity of the components and the desired properties of the dry composition. In general, the weight ratio of the process residue comprising alum to the acid to the material comprising reaction aluminum ranges from about 1.0 to 0.2 to 0.02 (i.e., 1:0.2:0.02) to about 1.0 to 2.0 to 0.4 (i.e., 1:2:0.4). In some embodiments, the weight ratio of the process residue comprising alum to the acid to the material comprising reaction aluminum may range from about 1:0.5:0.05 to about 1:1.5:0.2. In specific embodiments in which the process residue comprising alum is alum process residue (APR), the acid is sulfuric acid, and the material comprising reaction aluminum is bauxite, the ratio of APR to sulfuric acid to bauxite may range from about 1:0.6:0.06 to about 1:1.4:0.16.

(b) Mixing Step

The first step of the process comprises a mixing step during which the components of the composition are combined and mixed. The ingredients may be combined in any order with concurrent mixing or the ingredients may be combined in any order followed by subsequent mixing. In some embodiments, therefore, the process residue comprising alum and the acid may be mixed together prior to addition of the material comprising reactive aluminum. For example, the acid (or aliquots thereof) may be added to the process residue comprising alum while mixing or the mixing may commence after the one or more additions of the acid. Alternatively, the process residue comprising alum may be added to the acid with or without concurrent mixing. In other embodiments, the process residue comprising alum and the material comprising reactive aluminum may be mixed together prior to addition of the acid with or without concurrent mixing. Additionally, each component may be added in one aliquot or in multiple aliquots. Furthermore, any optional additional ingredient may be added at any time during the mixing step.

Prior to combining and mixing, the process residue comprising alum may be broken into smaller sized fragments. For example, press cakes of the process residue or sheets of the process residue may be broken, crushed, pulverized, or ground into smaller sized fragments or pieces. For example, large pieces of the process residue may be broken into smaller sized pieces with a stone crusher, a jaw crusher, a cone crusher, or a vertical shaft impact (VSI) crusher. Similarly, the material comprising reactive aluminum may be broken into fragments of smaller sizes. In embodiments in which the material comprising reactive aluminum is bauxite, the bauxite may be crushed or broken into smaller sized fragments with a stone crusher, a jaw crusher, a cone crusher, or a VSI crusher.

The mixing of the ingredients may be performed manually or mechanically. In specific embodiments, the mixing may be conducted using a mechanical mixer. The mechanical mixer by be a paddle mixer, a blade mixer, a ribbon mixer, a screw mixer, a horizontal mixer, a swing mixer, a blend mixer, an agitator mixer, a planetary mixer, a conical mixer, a double cone blender, a drum blender, a V blender, a screw blender, a high shear mixer/granulator, or another suitable mixing device.

The mixing step generally is performed at ambient or room temperature. Contact between the acid and the other ingredients, however, typically results in the generation of heat. In general, the temperature of the mixture increases to a temperature of less than about 100° C. In some embodiments, the maximum temperature of the mixture may be less than about 90° C., less than about 80° C., or less than about 70° C.

The duration of the mixing step can and will vary. In general, the mixture is mixed long enough to ensure formation of a uniform mixture. In some embodiments, the mixture that is formed is a slurry. Additionally, continued mixing of the mixture may help dissipate some of the heat generated during the mixing step and/or remove water from the mixture. In some embodiments, the mixture may be mixed for a period ranging from about 0.5 hr to about 2 hr, from about 2 hr to about 4 hr, from about 4 hr to about 8 hr, from about 8 hr to about 18 hr, or from about 18 hr to about 24 hr.

(c) Drying Step

The final step of the process comprises a drying step during which water is removed from the mixture to produce the dry composition. In certain embodiments, the drying process may be an air dry process, wherein drying of the mixture is facilitated by fans, blowers, air movers, driers, and/or other such devices. In other embodiments, the drying process may be a thermal drying process, wherein the mixture may be dried using a conveyer drier or cooler, drying oven, convection drier, drying chamber, rotary drier, dry room, and/or continuous tray drier. In still other embodiments, the drying process may be a mechanical de-watering process, wherein water is removed by the mixture using an industrial press, centrifugation, or filtration. In some embodiments, the mixture from the first step may be spread into a layer to facilitate the drying process.

In general, the drying process proceeds until the composition has a water content of about 10% or less as detailed above in section (I)(a)(iv).

(d) Optional Granulation Step

In some embodiments, the process further comprises a granulation step in which granules of the dried composition are generated. The average size of the particles is detailed above in section (I)(c). The granules of the dry composition may be formed by crushing, grinding, milling, dry granulating, and/or other suitable means known in the art. The granules may be sieved to collect granules of the desired size range.

(III) Methods for Using the Dry Compositions

A further aspect of the present disclosure provides methods for using the dry compositions detailed above. Non-limiting examples of suitable uses include acidifying animal litters, acidifying the floors of animal facilities, reducing ammonia volatilization in animal facilities, improving air quality in animal facilities, reducing odor from animal facilities, reducing moisture levels in animal litters, reducing the levels of litter microorganisms, reducing the amount of energy needed to heat or ventilate animal facilities, increasing the nitrogen content of animal litters for improved fertilizer value, reducing the runoff of soluble phosphorous from animal litters, reducing animal stress, reducing animal infections, increasing animal weight gain, increasing animal productivity, improving feed conversion ratios, and improving the working environment of animal facility workers.

In general, the methods comprise applying the dry compositions to suitable surfaces to form treated surfaces. Suitable surfaces include those of animal litter and/or the floors (or pads) of animal facilities. Animal litters comprise bedding material, animal wastes, and spilled feed. The floors of animal facilities are in contact or will be in contact with animal wastes (or the litter comprising animal wastes). It well known that the organic nitrogen in animal wastes (i.e., urea or uric acid) can be converted to ammonia by microorganisms. Formation of ammonia is favored under alkaline conditions (i.e., higher pH levels) and elevated temperatures.

In some embodiments, the method of use comprises treating an animal facility, wherein the method comprises applying the dry composition to a surface of the animal facility to form a treated animal facility. In other embodiments, the method of use comprises treating a surface in contact with or which will contact animal wastes, wherein the method comprises applying the dry composition to the surface to form a treated surface. In further embodiments, the method of use comprises treating an animal litter, wherein the method comprises applying the dry composition to the animal litter to form a treated animal litter.

Because the dry compositions comprise proton sources, application of the dry compositions lowers the pH of the surfaces to which the composition is applied. In general, application of the dry composition lowers the pH of the surface to a value of less than about 7.0. In some embodiments, the dry composition lowers the pH of the surface to a value of less than about 6.0, less than about 5.0, less than about 4.0, less than about 3.0, or less than about 2.0. Techniques for measuring pH are well known in the art. In general, the surface treated with the dry composition has a lower pH than a comparable untreated surface.

The acidification of the treated surfaces prevents volatilization of ammonia that may be formed from animal wastes present on or near the treated surfaces. That is, protons bind volatile ammonia ($NH_3$) and form non-volatile ammonium ($NH_4^+$). Ammonium is a highly reactive ion that bonds with sulfates, nitrates, phosphates, or other anions to form ammonium salts. The presence of ammonium salts in animal litters improves their nutrient value use as fertilizers. Thus, animal litters treated with the dry composition have higher levels of bound nitrogen than untreated litters. Accordingly, the treated litters have increased value as fertilizers as compared to untreated litters. Furthermore, animal litters treated with the dry composition have lower levels of soluble phosphorus than untreated litters. Thus, the treated animal litters have less soluble phosphorous runoff than untreated animal litters.

Inhibiting ammonia volatilization also reduces the levels of airborne ammonia in animal facilities. The generally recognized acceptable level of airborne ammonia in animal facilities is about 25 parts per million (ppm) or less. In some embodiments, the level of ammonia in the animal facility may be less than about 25 ppm, less than about 20 ppm, less than about 15 ppm, less than about 10 ppm, less than about 5 ppm, or less than about 1 ppm. Ammonia levels may be monitored and measured by a variety of means. Suitable means include ammonia meters, ammonia detection devices, ammonia sensors, ammonia gas monitors, colorimetric test strips, colorimetric paper, passive colorimetric tube detectors for ammonia, active colorimetric tubes for ammonia, and other detection means well-known in the art. In general, animal facilities treated with the dry composition have lower levels of airborne ammonia than comparable untreated animal facilities.

Reducing airborne ammonia levels in animal facilities, therefore, improves air quality in animal facilities. Improved air quality (i.e., low ammonia levels) improves the quality of life for animals housed in the animal facility and reduces the physiological stress of the animals. Animals with reduced stress generally have increased weight gain, better feed conversion ratios, increased productivity (e.g., increased egg production, increased milk production, etc.) and/or fewer infections or diseases than stressed animals. Improved air quality (i.e., low ammonia levels) also provides better working conditions for the animal facility workers. Reducing the levels of airborne ammonia may also reduce the amount of energy needed to ventilate and/or heat the animal facilities. Lastly, inhibiting ammonia volatilization may also reduce odor from animal litter and/or animal facilities.

The pH reduction on the treated surfaces may also create unfavorable environments for the propagation of microorganisms that contribute to ammonia formation. Thus, less ammonia may be formed on or near surfaces treated with the dry compositions. Additionally, the acidification of the surface may create conditions unfavorable for the proliferation of undesirable microorganisms that can infect or cause diseases in the animals housed in the animal facility.

As detailed elsewhere, the dry compositions comprise immediate and delayed sources of protons. Accordingly, the dry compositions disclosed herein generally have a rapid onset of activity as well as a prolonged or extended duration of activity. Protons are immediately provided by the acid included in the compositions. Thus, the dry compositions disclosed herein do not require water for activation. Protons also can be generated over extended periods of time from the delayed sources of protons (i.e., materials comprising alum and/or reactive aluminum) via hydrolysis reactions. Water for these hydrolysis reactions is provided by the animal litter. Thus, the dry composition is able to reduce moisture levels in animal litters. Accordingly, animal litters treated with the dry composition have lower levels of moisture than untreated animal litters.

The onset of activity and the duration of activity of the dry compositions can and will vary depending, for example, on the application rate, ventilation rate, ambient temperature, depth of litter layer, and so forth. In some embodiments, the dry compositions may reduce pH and/or reduce ammonia levels within about 1 hour, within about 6 hours, within 12 hours, or within 24 hours of application. In other embodiments, the dry compositions may reduce pH and/or control ammonia to levels of 25 ppm or less for at least about 7 days, at least about 9 days, at least about 11 days, at least about 13 days, at least about 15 days, at least about 17 days, at least about 19 days, at least about 21 days, or longer than about 21 days.

The amount of the dry composition applied to an animal litter layer or floor of an animal facility can and will vary depending, for example, upon the temperature and amount of ventilation in the animal facility, the age and/or moisture content of the litter layer, and so forth. In various embodiments, the dry composition may be applied at a rate that ranges from about 0.5 to 2 lbs per 100 $ft^2$, from about 2 to 4 lbs per 100 $ft^2$, from about 4 to 6 lbs per 100 $ft^2$, from about 6 to 8 lbs per 100 $ft^2$, from about 8 to 10 lbs per 100 $ft^2$, from about 10 to 12 lbs per 100 $ft^2$, from about 12 to 15 lbs per 100 $ft^2$, from about 15 to 20 lbs per 100 $ft^2$, or from about 20 to 30 lbs per 100 $ft^2$ of surface area. The dry composition may be applied to the surface using a spinner spreader, a broadcast spreader, a drop spreader, a lime spreader, a litter spreader, a fertilizer spreader, or any other spreader know in the field.

In some embodiments, the dry composition may be applied to an animal litter surface or animal facility floor surface without a preheating step. Ammonia production is promoted by high temperatures and high pH (i.e., alkaline conditions). Thus, temporarily increasing the temperature of the animal facility prior to animal placement may promote ammonia generation and volatilization from the litter layer during the "burn off" period. Because the dry compositions disclosed herein have immediate activity, a burn off period is not required prior to application of the dry composition. In other embodiments, the dry composition may be applied to an animal litter surface or animal facility floor surface after a preheating step. In general, however, the dry composition is typically applied to the desired surface up to several days prior to animal placement to ensure that the levels of ammonia in the enclosure are 25 ppm or less at the time of animal placement.

The dry compositions disclosed herein may be used in a variety of animal facilities. In some embodiments, the animal facility may house livestock animals such as poultry (e.g., chickens, turkeys, ducks, geese, etc.), cattle (e.g., dairy, beef, veal, etc.), pigs, sheep, and goats. In other embodiments, the animal facility may be used by companion animals such as cats, dogs, horses, rodents (e.g., mice, rats, hamsters, gerbils, guinea pigs), and the like. In other embodiments, the animal facility may be used by zoo animals such as monkeys, chimpanzees, lions, tigers, elephants, giraffes, and so forth. In certain embodiments, the animal facility may be a poultry facility. In specific embodiments, the animal facility may be a chicken facility.

Definitions

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

The term "alum" refers to aluminum sulfate.

As used herein, the term "ammonia control" refers to means for maintaining atmospheric ammonia levels at 25 ppm or less by the inhibition of ammonia volatilization.

An "immediate source of protons" refers to a compound (i.e. a Brønsted-Lowry acid) that readily can donate a proton to a base.

As used herein, a "delayed source of protons" refers to a compound that can generate protons during its hydrolysis.

The term "animal litter" as used herein refers to a mixture of animal excreta, spilled feed, and bedding material.

The term "poultry litter," as used herein, refers to a mixture of poultry excreta, spilled feed, feathers, and material used as bedding in poultry operations. Common bedding materials include wood shavings, sawdust, peanut hulls, shredded sugar cane, straw, and other dry, absorbent, low-cost organic materials. The bedding materials help absorb moisture, thereby limiting the production of ammonia and harmful pathogens.

As used herein, the term "reactive aluminum" refers to aluminum oxide ($Al_2O_3$), aluminum hydroxide ($Al(OH)_3$), aluminum oxide hydroxide ($AlO(OH)$), or combinations thereof.

As various changes could be made in the above-described animals, cells and methods without departing from the scope of the invention, it is intended that all matter contained in the above description and in the examples given below, shall be interpreted as illustrative and not in a limiting sense.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Preparation of Batch 1

To 200 lbs of alum process residue (APR) was added 135 lbs of 93% sulfuric acid. The mixture was mixed until no clumps were visible. The mixture was then spread into a thin layer and dried with a fan until it was dry enough to be crumbly. The final product contained 29.2% free acid and 3.97% $Al_2O_3$ to yield a total sulfate content of 40.4%.

Example 2. Preparation and Field Testing of Batch 2

About 42 lbs of high clay alumina (HCA) was mixed with 25 lbs of 93% sulfuric acid. The mixture was then spread into a thin layer and dried with a fan. The dry composition was still a little tacky.

The effectiveness of the dry composition to control ammonia levels in a poultry barn was compared to that of a commercial poultry litter treatment product (sodium bisulfate). Both were applied to broiler litter at a rate of 50 lbs per 500 ft$^2$ (the dry composition was spread by hand). Ammonia levels were measured with an ammonia meter (Drager Pac 3) and colorimetric ammonia gas detection tubes (Rae tubes). Table 1 presents the ammonia levels under both conditions over time. Both litter amendments reduced ammonia levels within 30 min of application and maintained ammonia levels at acceptable levels for at least 3 days.

TABLE 1

Field Trial - Ammonia Control

| Condition | Dry Composition #2 | Sodium Bisulfate |
|---|---|---|
| Pre treat | 104 ppm | 90 ppm |
| 30 min post treat | 35 ppm | 35 ppm |
| 6 hr post treat | 27.5 ppm | 30 ppm |
| 10.5 hr post treat | 21 ppm | 21 ppm |
| Day 3 | 23 ppm (meter) | 30 ppm (meter) |
|  | 40 ppm (tube) | 40 ppm (tube) |
| Day 6 | 43 ppm (meter) | 45 ppm (meter) |
|  | 35 ppm (tube) | 30 ppm (tube) |

Example 3. Preparation and Field Testing of Batch 3

About 200 lbs of APR (having ~30% moisture) from an industrial press was placed in the mud mixer. The press cake of APR was broken into smaller pieces no larger in size than golf balls. To the mixer was added 135 lbs of 93% sulfuric acid. The mixer was started and the ingredients formed a slurry almost immediately. The slurry was mixed for 15 min. Then, 15 lbs of bauxite was added to the mixer, and the slurry was mixed for another 15 min. The slurry was poured into a layer, and left to dry overnight. The yield of the dry product was about 300 lbs, and it contained 6.9% $Al_2O_3$, 9.0% $H_2SO_4$, for a total sulfate content of 34.1%. The dry composition was milled into smaller sized particles.

A field trial was conducted to compare the ammonia control efficacy of the dry composition to that of Al+Clear liquid (A7) under normal broiler house conditions. A7 was applied at a rate of 25 gallons per 1000 ft$^2$ and the dry composition was applied at a rate of 83 lbs per 1000 ft$^2$. The litter amendments were applied three days prior to bird placement. Minimum ventilation at placement was 28 sec. [on]: 280 sec. [off]. The test house ventilation was increased to 30 sec. [on]: 270 sec. [off] on the second day after placement (because the ammonia levels exceeded 25 ppm). Ammonia measurements were taken approximately at the same time each day using a Drager Pac 3 ammonia meter. Table 2 presents the ammonia levels after bird placement (day 0). Both amendments reduced ammonia levels.

TABLE 2

Field Trial - Ammonia Control

|  | Dry Composition #3 | A7 |
|---|---|---|
| Day 0 | 9 ppm | 2 ppm |
| Day 1 | 29 ppm | 4 ppm |
| Day 2 | 18 ppm | 3 ppm |
| Day 3 | 17 ppm | 11 ppm |
| Day 7 | 12 ppm | 10 ppm |
| Average | 17 ppm | 6 ppm |

Example 4. Preparation and Field Testing of Batch 4

About 2,340 lbs of APR (having ~30% moisture) from an industrial press was placed in the mud mixer. To the mixer was added 2,800 lbs of 93% sulfuric acid. The mixer was started, a slurry was formed, and the slurry was mixed for 120 min. Then, 340 lbs of bauxite was added to the mixer, and the slurry was mixed for another 60 min. Around 1,200 lbs of water was added to the mixture. The slurry was poured into a layer, and left to dry overnight. The yield of the dry product was about 4,738 lbs, and it contained 11.3% $Al_2O_3$, 6.5% $H_2SO_4$, for a total sulfate content of 40.1%. The dry composition was milled into smaller sized particles.

A field trial was conducted to compare the ammonia control efficacy of the dry composition to that of sodium bisulfite or a blend of 50 wt % sodium bisulfite and 50 wt % Al+Clear alum under normal broiler house conditions. Each litter amendment was applied at a rate of 100 lbs per 1000 ft$^2$ and three days prior to bird placement. Ammonia measurements were taken approximately at the same time each day using a Drager Pac 3 ammonia meter. The number of dead birds was recorded each day. Table 3 presents the ammonia levels after bird placement (day 0), as well as the bird mortality. Dry composition #4 was more effective than sodium bisulfite at reducing ammonia levels and mortality.

TABLE 3

| | Field Trial - Ammonia Control | | | | | |
|---|---|---|---|---|---|---|
| | Dry composition #4 | | Sodium Bisulfite | | Blend | |
| | NH$_3$ (ppm) | Morality | NH$_3$ (ppm) | Morality | NH$_3$ (ppm) | Morality |
| Day 1 | 6 | 97 | 7 | 90 | 7 | 103 |
| Day 2 | 23 | 50 | 7 | 44 | 9 | 60 |
| Day 3 | 18 | 70 | 9 | 79 | 4 | 68 |
| Day 4 | 30 | 83 | 14 | 80 | 3 | 80 |
| Day 5 | 28 | 91 | 40 | 187 | 28 | 89 |
| Day 6 | 30 | 97 | 44 | 73 | 30 | 50 |
| Day 7 | 26 | 90 | 35 | 130 | 21 | 50 |
| Day 8 | 24 | | 35 | | 21 | |
| Mean ppm | 23.13 | | 23.88 | | 15.38 | |
| % 7 day mortality | | 1.87 | | 2.27 | | 1.66 |

Example 5. Ammonia Control—Laboratory Tests

Used litter was acquired from a commercial broiler farm and transported to the testing facility in plastic barrels. Equal amounts of litter were weighed into 3 ft$^2$ plastic tubs at a depth of 4 to 5 in. The tubs were stored uncovered in a poultry rearing facility, and environmental conditions were controlled to mimic conditions that would be experienced in a commercial broiler house. After a 48 hr settling and purging period, each tub was sampled in 2 locations for ammonia volatilization. This initial ammonia sampling served as the baseline measurement (day −1). The following litter amendments were tested: No treatments, sodium bisulfite, Al+Clear alum, dry composition #3, and dry composition #4. The litter amendments were applied at a rate of 1 pound per 10 ft$^2$; and each treatment was tested in quadruplicate. Ammonia measurements were then taken at the appropriate timeframe following product application that would represent chick placement under commercial conditions (day 0). Starting at day 1, the litter in each container was raked daily to simulate litter disturbance that would naturally occur with broiler movement. Additionally, water was added on a daily basis to the litter to simulate fecal moisture deposition.

Figure 1:
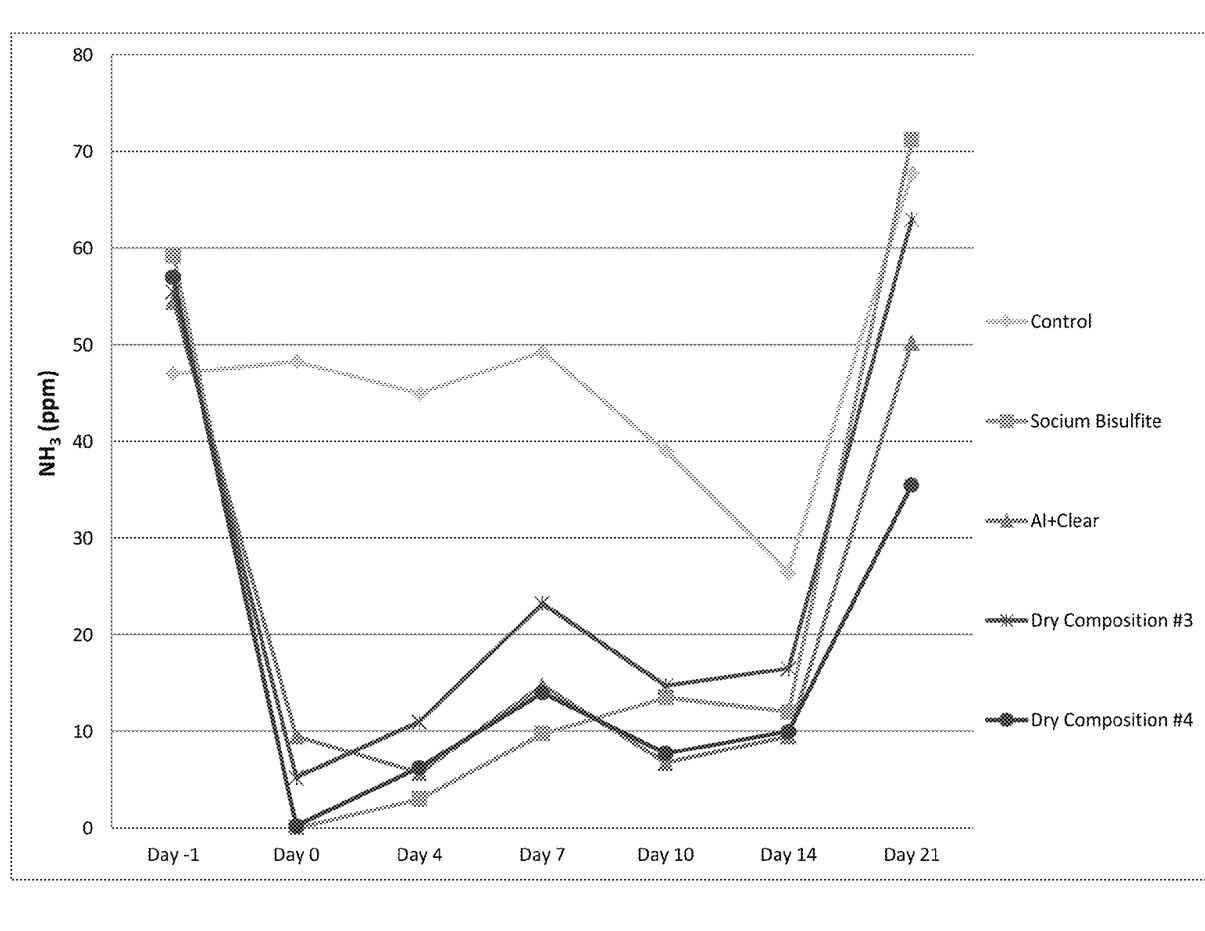
FIG. 1 illustrates ammonia control under laboratory conditions of the indicated litter amendments. Plotted in the level of ammonia in ppm at selected days over the course of 21 days. Dry composition #4 provided immediate and extended ammonia control.

Volatilization of ammonia from the litter was assessed by placing a 14 inch-diameter, dome-shaped stainless steel chamber over the litter and measuring the ammonia accumulated in the chamber headspace (static chamber method). Each chamber is equipped with a small DC fan to prevent gas stratification within the chamber. Headspace gases were sampled every 6 minutes for a 24 minute period using a SAM IV ammonia monitor (infrared photometer). As previously mentioned, ammonia measurements were taken prior to litter treatment to establish baseline measurements, followed by ammonia measurements on day 0 (simulated bird placement) and on day 4, 7, 14, and 21 post-simulated bird placement. The data are presented in Table 4 and FIG. 1. At 21 days, dry composition #4 maintained the lowest ammonia levels. Thus, the dry composition provides immediate and extended ammonia control.

TABLE 4

| | Laboratory Test. | | | | | | |
|---|---|---|---|---|---|---|---|
| | NH$_3$ Level (ppm) | | | | | | |
| | Day −1 | Day 0 | Day 4 | Day 7 | Day 10 | Day 14 | Day 21 |
| Control | 47.0 | 48.25 | 45.0 | 49.25 | 39.0 | 26.5 | 67.75 |
| Sodium bisulfite | 59.25 | 0 | 3.0 | 9.75 | 13.5 | 12.0 | 71.25 |
| Al + Clear | 54.5 | 9.5 | 5.75 | 14.75 | 5.75 | 9.5 | 50.25 |
| Dry composition #3 | 55.5 | 5.25 | 11.0 | 23.25 | 14.75 | 16.5 | 63.0 |
| Dry composition #4 | 57.0 | 0.25 | 6.25 | 14.0 | 7.75 | 10.0 | 35.5 |

Example 6. Preparation of Batch 5

About 2,000 lbs of APR (having ~33% moisture) from an industrial press was placed in the mud mixer. To the mixer was added 2,000 lbs of 93% sulfuric acid. The mixer was started, a slurry was formed, and the slurry was mixed for 120 min. Then, 180 lbs of bauxite was added to the mixer, and the slurry was mixed for another 60 min. Around 180 lbs of water was added to the mixture. The slurry was poured into a layer, and left to dry overnight. The yield of the dry product was about 4,190 lbs, and it contained 12.1% Al$_2$O$_3$, 11.1% H$_2$SO$_4$, for a total sulfate content of 44.3%. The dry composition was milled into smaller sized particles.

What is claimed is:

1. A dry composition comprising (a) a process residue comprising alum, (b) an acid, and (c) a material comprising aluminum oxide, aluminum hydroxide, aluminum oxide hydroxide, or combination thereof, wherein (b) provides an immediate source of protons, and each of (a) and (c) provides a delayed source of protons, and wherein the dry composition contains about 30% to about 60% by weight of (a), about 3% to about 20% by weight of (b) in a free form, and about 1% to about 15% by weight of (c).

2. The dry composition of claim 1, wherein the process residue comprising alum is chosen from alum process residue, alum mud, high clay alumina, or a combination thereof, and comprises from about 0.5% to about 10% of alum by weight of the process residue.

3. The dry composition of claim 1, wherein the acid is chosen from sulfuric acid, hydrochloric acid, hydrobromic acid, hydroiodic acid, nitric acid, phosphoric acid, perchloric acid, chloric acid, fluorosulfuric acid, fluoroboric acid, hexafluorophosphoric acid, methanesulfonic acid, ethanesulfonic acid, benzenesulfonic acid, p-toluenesulfonic acid, trifluoromethanesulfonic acid, or a combination thereof.

4. The dry composition of claim 1, wherein the material comprising aluminum oxide, aluminum hydroxide, aluminum oxide hydroxide, or combination thereof is chosen from bauxite, aluminum ore, high alumina clay, aluminum silicate, gibbsite, boehmite, diaspore, aluminum trihydrate, alumina, calcinated alumina, corundum, or a combination thereof.

5. The dry composition of claim 1, which is prepared by mixing the process residue comprising alum, the acid, and the material comprising aluminum oxide, aluminum hydroxide, aluminum oxide hydroxide, or combination thereof to form a mixture; and drying the mixture to form the dry composition, and wherein the process residue comprising alum, the acid, and the material comprising reactive aluminum are mixed together at a weight ratio from about 1:0.2:0.02 to about 1:2:0.4.

6. The dry composition of claim 1, which comprises from about 3% to about 20% of aluminum oxide, from about 4% to about 18% of in a free form, from about 30% to about 50% of anion from the acid, and about 10% or less of water by weight of the dry composition.

7. The dry composition of claim 1 having a pH of at least 1.

8. The dry composition of claim 1, which is a granular material.

9. The dry composition of claim 1, further comprising additional alum, aluminum hydrate, aluminum clay, lime, soda ash, caustic potash, caustic soda, or a combination thereof.

10. The dry composition of claim 1, wherein (a) is alum process residue (APR) comprising from about 1% to about 6% of alum, (b) is sulfuric acid, and (c) is bauxite.

11. The dry composition of claim 10, which is prepared by mixing APR, sulfuric acid, and bauxite to form a mixture; and drying the mixture to form the dry composition, and wherein APR, sulfuric acid, and bauxite are mixed together at a weight ratio from about 1:0.5:0.05 to about 1:1.5:0.2.

12. The dry composition of claim 11, wherein APR and sulfuric acid are first mixed together, and then bauxite is mixed into the mixture.

13. The dry composition of claim 10, which comprises from about 5% to about 16% of aluminum oxide, from about 5% to about 16% of sulfuric acid, from about 35% to about 45% of sulfate, and about 5% or less of water by weight of the dry composition.

14. The dry composition of claim 10 having a pH from about 1 to about 2.

15. A method for treating an animal facility, the method comprising applying a dry composition to a surface of the animal facility to form a treated animal facility, wherein the dry composition comprises about 30% to about 60% by weight of a process residue comprising alum, about 3% to about 20% by weight of an acid in free form, and about 1% to about 15% by weight of a material comprising aluminum oxide, aluminum hydroxide, aluminum oxide hydroxide, or combination thereof.

16. The method of claim 15, wherein the surface of the animal facility is a litter surface or a floor surface of the animal facility.

17. The method of claim 15, wherein the treated animal facility has a lower level of airborne ammonia than an untreated animal facility.

18. The method of claim 15, wherein the treated animal facility litter has a lower pH level, a lower moisture level, a higher nitrogen level, a lower soluble phosphorous level, a lower level of microorganisms, or a combination thereof than an untreated animal facility litter.

19. The method of claim 15, wherein the treated animal facility houses animals having less physiological stress, increased weight gain, improved performance, or a combination thereof relative to animals in an untreated facility.

20. The method of claim 15, wherein the process residue comprising alum is chosen from alum process residue, alum mud, high clay alumina, or a combination thereof, and comprises from about 0.5% to about 10% of alum by weight of the process residue.

21. The method of claim 15, wherein the acid is chosen from sulfuric acid, hydrochloric acid, hydrobromic acid, hydroiodic acid, nitric acid, phosphoric acid, perchloric acid, chloric acid, fluorosulfuric acid, fluoroboric acid, hexafluorophosphoric acid, methanesulfonic acid, ethanesulfonic acid, benzenesulfonic acid, p-toluenesulfonic acid, trifluoromethanesulfonic acid, or a combination thereof.

22. The method of claim 15, wherein the material comprising aluminum oxide, aluminum hydroxide, aluminum oxide hydroxide, or combination thereof is chosen from bauxite, aluminum ore, high alumina clay, aluminum silicate, gibbsite, boehmite, diaspore, aluminum trihydrate, alumina, calcinated alumina, corundum, or a combination thereof.

23. The method of claim 15, wherein the dry composition is prepared by mixing the process residue comprising alum, the acid, and the material comprising aluminum oxide, aluminum hydroxide, aluminum oxide hydroxide, or combination thereof to form a mixture; and drying the mixture to form the dry composition, and wherein the process residue comprising alum, the acid, and the material comprising aluminum oxide, aluminum hydroxide, aluminum oxide hydroxide, or combination thereof are mixed together at a weight ratio from about 1:0.2:0.02 to about 1:2:0.4.

24. The method of claim 15, wherein the dry composition comprises from about 3% to about 20% of aluminum oxide, from about 4% to about 18% of the acid in a free form, from about 30% to about 50% of anion from the acid, and about 10% or less of water by weight of the dry composition.

25. The method of claim 15, wherein the dry composition further comprises additional alum, aluminum hydrate, aluminum clay, lime, soda ash, caustic potash, caustic soda, or a combination thereof.

26. The method of claim 15, wherein the dry composition is a granular material.

27. The method of claim 15, wherein the animal facility is a poultry facility.

28. A method for treating a surface that contacts or will contact animal wastes, the method comprising applying a dry composition to the surface to form a treated surface, wherein the dry composition comprises about 30% to about 60% by weight of a process residue comprising alum, about 3% to about 20% by weight of an acid in free form, and about 1% to about 15% by weight of a material comprising aluminum oxide, aluminum hydroxide, aluminum oxide hydroxide, or combination thereof.

29. The method of claim 28, wherein the surface is an animal litter surface or an animal facility floor surface.

30. The method of claim 28, wherein the treated surface has a lower pH than an untreated surface.

31. The method of claim 28, wherein volatilization of ammonia is reduced on the treated surface as compared to an untreated surface.

32. The method of claim 28, wherein the process residue comprising alum is chosen from alum process residue, alum mud, high clay alumina, or a combination thereof, and comprises from about 0.5% to about 10% of alum by weight of the process residue.

33. The method of claim 28, wherein the acid is chosen from sulfuric acid, hydrochloric acid, hydrobromic acid, hydroiodic acid, nitric acid, phosphoric acid, perchloric acid, chloric acid, fluorosulfuric acid, fluoroboric acid, hexafluorophosphoric acid, methanesulfonic acid, ethanesulfonic acid, benzenesulfonic acid, p-toluenesulfonic acid, trifluoromethanesulfonic acid, or a combination thereof.

34. The method of claim 28, wherein the material comprising aluminum oxide, aluminum hydroxide, aluminum oxide hydroxide, or combination thereof is chosen from bauxite, aluminum ore, high alumina clay, aluminum silicate, gibbsite, boehmite, diaspore, aluminum trihydrate, alumina, calcinated alumina, corundum, or a combination thereof.

35. The method of claim 28, wherein the dry composition is prepared by mixing the process residue comprising alum, the acid, and the material comprising aluminum oxide, aluminum hydroxide, aluminum oxide hydroxide, or combination thereof to form a mixture; and drying the mixture to form the dry composition, and wherein the process residue comprising alum, the acid, and the material comprising aluminum oxide, aluminum hydroxide, aluminum oxide hydroxide, or combination thereof are mixed together at a weight ratio from about 1:0.2:0.02 to about 1:2:0.4.

36. The method of claim 28, wherein the dry composition comprises from about 3% to about 20% of aluminum oxide, from about 4% to about 18% of the acid in a free form, from about 30% to about 50% of anion from the acid, and about 10% or less of water by weight of the dry composition.

37. The method of claim 28, wherein the dry composition further comprises additional alum, aluminum hydrate, aluminum clay, lime, soda ash, caustic potash, caustic soda, or a combination thereof.

38. The method of claim 28, wherein the dry composition is a granular material.

39. The method of claim 28, wherein the surface is a poultry litter surface or a poultry facility floor surface.

40. A method for treating an animal litter, the method comprising applying a dry composition to the animal litter to form a treated animal litter, wherein the dry composition comprises about 30% to about 60% by weight of a process residue comprising alum, about 3% to about 20% by weight of an acid in free form, and about 1% to about 15% by weight of a material comprising aluminum oxide, aluminum hydroxide, aluminum oxide hydroxide, or combination thereof.

41. The method of claim 40, wherein the treated animal litter has a lower level of moisture, a higher level of nitrogen, a lower level of soluble phosphorus, a lower level of undesirable litter microorganisms, or a combination thereof than an untreated animal litter.

42. The method of claim 40, wherein the process residue comprising alum is chosen from alum process residue, alum mud, high clay alumina, or a combination thereof, and comprises from about 0.5% to about 10% of alum by weight of the process residue.

43. The method of claim 40, wherein the acid is chosen from sulfuric acid, hydrochloric acid, hydrobromic acid, hydroiodic acid, nitric acid, phosphoric acid, perchloric acid, chloric acid, fluorosulfuric acid, fluoroboric acid, hexafluorophosphoric acid, methanesulfonic acid, ethanesulfonic acid, benzenesulfonic acid, p-toluenesulfonic acid, trifluoromethanesulfonic acid, or a combination thereof.

44. The method of claim 40, wherein the material comprising aluminum oxide, aluminum hydroxide, aluminum oxide hydroxide, or combination thereof is chosen from bauxite, aluminum ore, high alumina clay, aluminum silicate, gibbsite, boehmite, diaspore, aluminum trihydrate, alumina, calcinated alumina, corundum, or a combination thereof.

45. The method of claim 40, wherein the dry composition is prepared by mixing the process residue comprising alum, the acid, and the material comprising aluminum oxide, aluminum hydroxide, aluminum oxide hydroxide, or combination thereof to form a mixture; and drying the mixture to form the dry composition, and wherein the process residue comprising alum, the acid, and the material comprising aluminum oxide, aluminum hydroxide, aluminum oxide hydroxide, or combination thereof are mixed together at a weight ratio from about 1:0.2:0.02 to about 1:2:0.4.

46. The method of claim 40, wherein the dry composition comprises from about 3% to about 20% of aluminum oxide, from about 4% to about 18% of the acid in a free form, from about 30% to about 50% of anion from the acid, and about 10% or less of water by weight of the dry composition.

47. The method of claim 40, wherein the dry composition further comprises additional alum, aluminum hydrate, aluminum clay, lime, soda ash, caustic potash, caustic soda, or a combination thereof.

48. The method of claim 40, wherein the dry composition is a granular material.

49. The method of claim 40, wherein the animal litter is a poultry litter.

* * * * *

UNITED STATES PATENT AND TRADEMARK OFFICE
CERTIFICATE OF CORRECTION

PATENT NO.         : 9,839,713 B2
APPLICATION NO.    : 14/714890
DATED              : December 12, 2017
INVENTOR(S)        : Rex Johns et al.

It is certified that error appears in the above-identified patent and that said Letters Patent is hereby corrected as shown below:

In the Claims

Column 15, Line 21, Claim 6: After "18% of" and before "in" insert --the acid--.

Signed and Sealed this
Sixth Day of February, 2018

Joseph Matal
*Performing the Functions and Duties of the
Under Secretary of Commerce for Intellectual Property and
Director of the United States Patent and Trademark Office*